United States Patent [19]

Thompson

[11] Patent Number: 5,718,862
[45] Date of Patent: Feb. 17, 1998

[54] SECONDARY SHAPING OF IONICALLY CROSSLINKED POLYMER COMPOSITIONS FOR MEDICAL DEVICES

[75] Inventor: Samuel Anthony Thompson, Wilmington, Del.

[73] Assignee: Hercules Incorporated, Wilmington, Del.

[21] Appl. No.: 639,071

[22] Filed: Apr. 24, 1996

[51] Int. Cl.⁶ .................................................. B29C 35/02
[52] U.S. Cl. ........................ 264/296; 264/294; 264/344; 264/347; 604/891.1; 604/265
[58] Field of Search ........................... 264/296, 294, 264/347, 343, 344; 604/265, 891.1

[56] References Cited

U.S. PATENT DOCUMENTS

| | | | |
|---|---|---|---|
| 3,271,496 | 9/1966 | Michaels | 264/232 |
| 3,361,858 | 1/1968 | Wichterle | 264/1 |
| 3,608,057 | 9/1971 | Bixler | 264/322 |
| 4,286,341 | 9/1981 | Greer et al. | 427/2 |
| 4,878,907 | 11/1989 | Okada et al. | 623/1 |
| 4,902,295 | 2/1990 | Walthall et al. | 623/11 |
| 4,941,870 | 7/1990 | Okada et al. | 600/36 |
| 4,997,443 | 3/1991 | Walthall et al. | 623/11 |
| 5,057,606 | 10/1991 | Garbe | 536/54 |
| 5,085,629 | 2/1992 | Goldberg et al. | 604/8 |
| 5,531,716 | 7/1996 | Luzio et al. | 604/265 |
| 5,531,735 | 7/1996 | Thompson | 604/891.1 |
| 5,541,304 | 7/1996 | Thompson | 536/20 |

FOREIGN PATENT DOCUMENTS

| | | |
|---|---|---|
| 0507604 | 4/1992 | European Pat. Off. |
| 0645150 | 3/1995 | European Pat. Off. |
| 6-6601 | 1/1994 | Japan . |

OTHER PUBLICATIONS

Kocvara et al., "Gel-Fabric Prosthesis of the Ureter," J. Biomed. Mat. Res., 1, pp. 325-336 (1967).

P. E. Ross, "Living Cure -Insulin-Secreting Implants Approach Human Testing", Sci. Am., Jun. 1993, pp. 18-23.

*Primary Examiner*—Jeffery R. Thurlow
*Attorney, Agent, or Firm*—Martin F. Sloan

[57] ABSTRACT

A method for preparing a medical device having the steps: (1) treating an ionically crosslinked hydrogel to strip a substantial amount of the ionic crosslinks while retaining the hydrogel in a desired shape; and (2) ionically re-crosslinking the treated hydrogel of step (1) while retaining the hydrogel in the desired shape. In an exemplary embodiment, a ureteral stent is made by mounting a length of extruded calcium or barium alginate tubing onto a shaping jig and performing secondary shaping to form coil-shaped ends by soaking the mounted tubing in a stirred potassium chloride bath, and then soaking it in a calcium chloride bath. The ends readily return after elastic deformation to their coil shapes, with the stent having a permanent memory imposed by the secondary shaping.

42 Claims, No Drawings

SECONDARY SHAPING OF IONICALLY CROSSLINKED POLYMER COMPOSITIONS FOR MEDICAL DEVICES

FIELD OF THE INVENTION

The invention relates to methods for the secondary shaping of hydrogels formed from ionically crosslinked polymer compositions to prepare medical devices, such as stents, that retain their configurations for long periods of time. The term "secondary shaping" refers to the shaping of the hydrogel after preliminary shaping or "preshaping" of an initially crosslinked polymer composition. Secondary shaping provides shape stability to medical devices prepared from ionically crosslinked polymer hydrogels, even when exposed to plasticizing environments such as sea water, brackish water, foods and beverages, blood, urine, feces, saliva, and bile.

BACKGROUND OF THE INVENTION

In mass production, many articles are fabricated from extruded or pultruded raw material stock. A secondary shape is often later imposed to the extruded or preformed stock to satisfy function.

For example, U.S. Pat. No. 3,361,858 to Wichterle discloses a process for forming a hydrogel contact lens by reshaping a xerogel by mechanical removal and swelling. Wichterle teaches that a contact lens may be prepared by preparing a lens blank from a xerogel, removing selected portions of the blank to form the shape of the desired lens on a reduced scale, and exposing the replica to an aqueous liquid until it swells to a state of osmotic equilibrium with physiological saline solution.

U.S. Pat. No. 3,608,057 to Bixler and Kendrick also describes a process that can be employed to prepare a contact lens from a composition containing an ionically crosslinked polymer. A contact lens may be prepared by replacing water in the composition through exposure to a nonvolatile organic plasticizer, machining or molding the plasticized composition into the desired form, and rehydrating the composition.

U.S. Pat. No. 5,531,716, the disclosure of which is incorporated by reference herein, which corresponds to European Patent Publication No. 0 645 150. A1, discusses a method whereby extruded, ionically crosslinked hydrogel compositions are shaped into medical devices after crosslinking. The crosslinked compositions can be preshaped, e.g., by extruding or molding a hydrogel composition, and then heat-shaped into a desired configuration, e.g., a stent having pigtail-shaped or coiled ends. For example, a ureteral stent can be made by extruding a polysaccharide-based hydrogel such as calcium alginate, and then shaping the ends into coils or pigtails, which prevent the stent from migrating after it is in place in the body.

Ureteral stents are used to facilitate drainage of urine from the kidney to the bladder. Other medical devices are often used to facilitate the flow of material, as, for example, in a vascular graft used to maintain blood flow. Typically, these medical devices have been made from durable, non-biodegradable materials such as metals, polyurethanes, polyacrylates, etc. These non-biodegradable, non-dissolvable medical devices usually must be removed via an invasive procedure after they have served their purpose, otherwise they remain in the body indefinitely. For those devices which remain in vivo, there are often medical complications such as inflammation and other foreign-body responses.

Devices have also more recently been prepared from biodegradable materials such as polyesters, polyanhydrides, and polyorthoesters. In U.S. Pat. No. 5,085,629, the use of a biodegradable polyester terpolymer of lactide, glycolide, and epsilon-caprolactone in a ureteral stent is disclosed. In that patent, biodegradable has been defined to include hydrolytic instability. These polymers undergo hydrolytic chain cleavage in the presence of water to form low molecular weight water-soluble species. The polyesters have been reported to undergo hydrolysis throughout the thickness of the device (homogeneous hydrolysis), while the polyanhydrides and polyorthoesters have been reported to hydrolyze from the surface (heterogeneous hydrolysis). There are several problems inherent to devices manufactured with these biodegradable materials. There is a significant loss of strength in the device prior to any significant weight loss. These devices may undergo failure into large pieces, which may occlude the vessel in which they have been deployed. Biodegradable devices that undergo surface hydrolysis may eventually reach a thin-skin configuration, which may also lead to vessel occlusion. Semicrystalline biodegradable materials have also been shown to leave insoluble crystalline residuals in the body for very long periods of time.

Polysaccharide-metal salt systems have been used for many years in biomedical applications. In European Patent Application No. 507 604 A2, an ionically crosslinked carboxyl-containing polysaccharide is used in adhesion prevention following surgery; the ionically crosslinked polysaccharide is left in vivo. Japanese Patent Publication No. 6-6601 (Jan. 26, 1994) describes a process for preparing a reinforced hydrogel by shaping a sodium alginate solution into a form such as granules or filaments using a solution containing calcium ions, and then treating the resulting gel with a solution containing barium ions to fortify it.

Hydrogels have been widely used in biomedical applications. U.S. Pat. Nos. 4,941,870, 4,286,341, and 4,878,907 disclose the use of a hydrogel as a coating on an elastomer base in a vascular prosthesis. This hydrogel remains in vivo. Kocavara et al. (J. Biomed. Mater. Res., vol. 1, 1967, pp. 325–336) have reported using an anastomosis ureteral prosthesis prepared from a poly(hydroxyethyl methacrylate) hydrogel reinforced with polyester fibers. This prosthesis is designed to be left in vivo.

U.S. Pat. Nos. 4,997,443 and 4,902,295 disclose the preparation of transplantable artificial pancreatic tissue from an alginic acid gel precursor, a matrix monomer, and pancreas cells with $Ca^{2+}$ ions and a matrix monomer polymerization catalyst. The calcium-alginic acid is used to provide mechanical integrity to the mixture while the matrix monomer is polymerized, after which the calcium-alginic acid is removed with citrate via calcium chelation to leave a porous matrix. This use of the chelate to dissolve the calcium-alginic acid takes place in vitro. The calcium-alginic acid functions as a processing aid, not as a structural member, in the final artificial-tissue device.

Polysaccharide-metal salt hydrogels have also been used to prepare tiny gel capsules containing pancreatic islet cells for the production of insulin. These capsules have been shown by workers at the Veterans Administration Wadsworth Medical center to effectively control insulin levels in diabetic dogs for two years (Scientific American, June 1992, pp. 18–22). These capsules remain in vivo.

U.S. Pat. No. 5,057,606 discloses a method and article useful for preparing polysaccharide hydrogels. These foamed and non-foamed gelled articles are prepared by mixing together a first component comprising a suspension of a water insoluble di- or tri-valent metal salt in an aqueous solution of a polysaccharide, with a second component comprising an aqueous solution of a water-soluble acid optionally to include the water-soluble polysaccharide. These gels remain in vivo.

U.S. Pat. No. 5,531,716, describes hydrogel medical devices that eliminate problems associated with the materials discussed above. Hydrolytic instability is not relied upon to facilitate dissolution. The devices are disintegrated upon demand through application of an agent that acts to remove ionic crosslinking species, which may be anionic (mono or poly) or cationic (mono or poly) in nature, via binding or displacement mechanisms. Triggered disintegration (breakdown of the device into small particulates and water-soluble components) eliminates the time uncertainty observed with bioerodible materials from one patient to the next. Methods for triggered disintegration include administering or triggering release of the disintegration agent through the diet, administering the agent directly onto the device in an aqueous solution, encapsulating the agent in the device, parenteral feeding, and enema. Disintegration occurs without significant swelling of the device. Thus, a medical device with excellent mechanical properties may be prepared by extruding into the form of tubing a hydrogel composition containing an ionically crosslinkable polymer, an ionic crosslinking agent, and a chemically triggerable disintegration agent, and then heat-shaping the ends of the tubing into coils or pigtails.

Other methods for heat-shaping articles are known. For instance, U.S. Pat. No. 3,271,496 to Michaels describes a method of shaping a plastic solid gel composition containing the water-insoluble reaction product of two initially water-soluble polyelectrolyte polymers that each has dissociable ionic groups of opposite charges. In the Michaels method, the solid composition of the two polymers is temporarily rendered plastic by immersion in an aqueous solution of an inorganic salt, such as calcium or sodium bromide, the resulting solid is at least partly dried, and then the solid is shaped into the desired form, e.g., by a well-known shaping procedure such as injection molding, melt casting, melt spinning, vacuum forming, and film laminating.

Although such shaped articles prepared from ionically crosslinked hydrogels, especially those shaped with the aid of heat, are very stable in many environments, they undesirably retain some memory of their preshaped configurations. When exposed to conditions conducive to molecular motion, a heat-shaped article tends to slowly return to its original, unstressed state. This tendency can be particularly undesirable in medical devices where the retention of a shape is important to proper performance, such as stents having elastically deformable features for retention in the body for the required period of time. Therefore, a method for preserving shape of a medical device, especially one having an elastically deformable retention feature, is desired.

SUMMARY OF THE INVENTION

An object of the invention is to provide a shaped medical device with improved shape retention. A related object is to provide a shaped medical device that better retains its shape for a long period of time, preferably in an essentially permanent fashion (i.e., over the usual life of the medical device).

Another object is to develop a convenient method for preparing a medical device, such as a pigtail stent, having an enhanced and elastically permanent shape memory after secondary shaping.

These and other objects of the invention have been achieved through a convenient method for permanently shaping ionically crosslinked compositions. In accordance with the invention, a stable, secondary shape is imposed, which substantially erases the memory of the original configuration (i.e., existing shape or preshape, e.g., extruded or straight configuration) of the crosslinked composition.

More specifically, the invention relates to a method for preparing a medical device comprising:

(1) treating an ionically crosslinked hydrogel to strip a substantial amount of the ionic crosslinks while retaining the hydrogel in a desired shape; and (2) ionically re-crosslinking the treated hydrogel of step (1) while retaining the hydrogel in the desired shape.

The ionically crosslinked hydrogel of step (1) preferably has a tubular preshape. Preferably, the ionically crosslinked hydrogel of step (1) is formed from calcium alginate. The re-crosslinking step (2) preferably comprises exposing the ionically crosslinked hydrogel to a re-crosslinking solution comprising water and a cationic crosslinker containing calcium, strontium, lead, copper, aluminum, iron, tin, or barium ions.

A preferred embodiment of the inventive method of preparing a medical device comprises:

(1) forming a hydrogel from a composition comprising an ionically crosslinkable polymer and an ionic crosslinking agent; and (2) forming the hydrogel into a secondary shape by steps comprising:

(a) imparting a secondary shape to the hydrogel, (b) stripping the hydrogel of crosslinks while retaining the secondary shape, and (c) re-crosslinking the hydrogel while retaining the secondary shape.

Preferably, in step (1) the hydrogel is formed into a length of tubing. The forming step (2) is preferably conducted at about room temperature.

Step (2)(a) preferably comprises mounting the hydrogel in a shaping device, which may include means for forming at least one coil or pigtail on the length of tubing. An exemplary shaping device is a shaping jig for forming pigtail stents. A relatively light to medium degree of tension is preferably used when loading the preshaped hydrogels onto shaping jigs. Although secondary shaping may be performed at higher temperatures (e.g., about 40°-100° C.), secondary shaping is preferably conducted at room temperature to produce devices having excellent mechanical strength and elasticity.

An additional, preferred exemplary shaping device for forming double pigtail stents consists of pairs of hollow, Teflon® coated, stainless steel cannula which have been bent into the desired pigtail or cross coil configuration. These cannula are inserted into the ends of the preshaped hydrogels, maintained during the shipping and re-cross linking steps, then removed.

In stripping step (2)(b), the mounted hydrogel is preferably immersed in an electrolyte solution having a concentration of electrolyte to achieve sufficient shipping. Preferably, the solution is about twenty-five percent by weight potassium, sodium, or lithium chloride. In an especially preferred embodiment, water and potassium chloride are present in the electrolyte solution in a concentration of about twenty-five percent by weight. The electrolyte solution may further comprise a plasticizer, e.g., urea, glycerol, or sorbitol. The electrolyte solution is preferably agitated or mixed during shipping, and is preferably at about room temperature.

The re-crosslinking step (2)(c) preferably comprises immersing the mounted hydrogel in a re-crosslinking solution comprising water and an ionic crosslinker. Where the polymer of the hydrogel composition is cationically crosslinkable, the ionic crosslinker preferably contains ions selected from barium, calcium, magnesium, strontium, boron, beryllium, aluminum, iron, copper, cobalt, lead, tin, and silver ions. Where the polymer of the hydrogel composition is anionically crosslinkable, the ionic crosslinker preferably contains ions selected from phosphate, citrate, borate, succinate, maleate, adipate, and oxalate ions. The re-crosslinking solution optionally further comprises urea, glycerol, sorbitol, an antiseptic, an antibiotic, or a fungicide.

In preferred embodiments, the shipping step (2)(b) comprises immersing a jig-mounted hydrogel in a solution of potassium, sodium, or lithium chloride, and the re-crosslinking step (2)(c) comprises immersing the mounted hydrogel in a re-crosslinking solution comprising water and a cationic crosslinker containing calcium, strontium, lead, copper, aluminum, iron, tin, or barium ions. More preferably, the cationic crosslinker contains calcium or barium ions.

A preferred hydrogel polymer is a polysaccharide, e.g., alginic acid, pectinic acid, hyaluronic acid, cellulose, chitosan, chitin, starch, dextran, heparin, chondroitin, cationic guar, cationic starch, carboxymethyl cellulose, carboxymethyl chitosan, carboxymethyl dextran, carboxymethyl starch, heparin sulfate, or chondroitin sulfate. More preferably, the polysaccharide is selected from alginic acid, pectinic acid, and hyaluronic acid, and their salts.

Preferred ionic crosslinking agents for the hydrogel composition include barium, calcium, strontium, and copper ions. In a preferred embodiment of the hydrogel composition, the polymer is alginic acid or a salt thereof, and the ionic crosslinking agent is barium or calcium ions.

The hydrogel composition optionally further comprises a disintegrating agent. The disintegrating agent is preferably selected from inorganic sulfates, inorganic phosphates, and magnesium ions.

The methods according to the invention are useful to essentially permanently alter the shape of not only extruded articles, but also any ionically crosslinked, preshaped article. The methods are used to advantageously prepare medical devices, such as stents, catheters, cannulas, plugs, and restrictors.

In a preferred embodiment, the method is used to prepare a stent having an elastic retention feature, such as a ureteral stent having one or more elastically deformable pigtail-shaped ends. Ureteral stents must be deformed by straightening out, e.g., over a guide wire or inside a scope, for insertion into the body. An elastically deformable shape that is sufficiently recoverable is key to the retention of the stent in the kidney and bladder.

Another embodiment of a medical device according to the invention is a biliary stent. A biliary stent also requires deformable retention features, such as flaps, that must be pressed flat during the insertion procedure, after which they recover and provide physical retention against the wall of the bile duct. The features must permanently retain their shape in an elastic manner until the in vivo dissolution or disintegration of the medical device is triggered or the medical device is otherwise removed from the body.

Other preferred embodiments and features of the invention will be apparent from the following detailed description of the invention.

DETAILED DESCRIPTION OF THE INVENTION

According to the invention, a preshaped hydrogel is subjected to secondary shaping. The term "hydrogel" indicates a water-insoluble, water-containing material. The hydrogel composition comprises at least one ionically crosslinkable polymer and at least one ionic crosslinking agent. The hydrogel composition may optionally contain other ingredients, e.g., a disintegration agent that allows for in vivo dissolution of the shaped hydrogel upon being triggered.

The ionically crosslinkable polymers may be anionic or cationic in nature. Exemplary polymers include carboxylic-, sulfate-, and amine-functionalized polymers. Among the anionic polymers that may be employed are polyacrylic acid, polymethacrylic acid, alginic acid, pectinic acid, carboxymethyl cellulose, hyaluronic acid, heparin, carboxymethyl starch, carboxymethyl dextran, heparin sulfate, and chondroitin sulfate. Among the cationic polymers that may be used are chitosan, cationic guar, cationic starch, and polyethylene amine or imine.

The polymer of the hydrogel composition is preferably a polysaccharide. Exemplary polysaccharide-based polymers include alginic acid, pectinic acid, hyaluronic acid, cellulose, chitosan, chitin, starch, dextran, heparin, chondroitin sulfate, cationic guar, cationic starch, and derivatives and salts thereof, such as carboxymethyl cellulose, carboxymethyl chitosan, carboxymethyl dextran, carboxymethyl starch, heparin sulfate, and chondroitin sulfate. Especially preferred polysaccharides are alginic acid, pectinic acid, and hyaluronic acid, and their salts.

The ionic crosslinking agents are generally categorized as anionic or cationic. Suitable cationic crosslinking agents include barium, calcium, magnesium, strontium, boron, beryllium, aluminum, iron, copper, cobalt, lead, and lo silver. Barium, calcium, strontium, and copper are preferred cations, with barium being especially preferred. Anionic crosslinkers are generally derived from polybasic organic or inorganic acids. Appropriate anionic crosslinking agents include phosphate, citrate, borate, succinate, maleate, adipate, and oxalate ions, with phosphate ions being preferred.

Optionally, the hydrogel composition may include or be exposed to a disintegration agent, which functions upon being triggered by displacing a crosslinking ion. Suitable disintegration agents include inorganic sulfates, ethylene diamine tetraacetic acid and ethylene dime tetraacetate, citrates, organic phosphates (e.g., cellulose phosphate), inorganic phosphates (e.g., pentasodium tripolyphosphate, mono- and di-basic potassium phosphate, sodium pyrophosphate), phosphoric acid, trisodium carboxymethyloxy succinate, nitrilotriacetic acid, maleic acid, oxalate, polyacrylic acid, and sodium, potassium, calcium, and magnesium ions. Inorganic sulfates, inorganic phosphates, and magnesium ions are preferred disintegration agents.

The disintegration agent may be added using an appropriate technique. Methods for triggered disintegration include administering or triggering release of the disintegration agent through the diet, administering the agent directly onto the device in an aqueous solution, encapsulating the agent in the device, parenteral feeding, and enema.

Examples of other optional ingredients or components of the hydrogel composition include treating agents or medicinal additives such as antiseptics, antibiotics, anticoagulants, pharmaceutical compounds, and the like.

The hydrogel composition has a preliminary shape, for example, a cylindrical or tubular preshape suitable for forming a stent. Preshaping may be achieved by an appropriate technique, e.g., by extruding or molding the hydrogel.

The preshaped hydrogel is then mounted onto a secondary shaping device, such as a jig. Preferably, the hydrogel is mounted under little or no tension.

The mounted hydrogel is then exposed to an electrolyte solution (e.g., by immersion or spraying) for an appropriate time and in an appropriate concentration to strip (i.e., remove, break, or displace) a sufficient amount of crosslinks. Suitable electrolyte solutions are those that will displace the crosslinking ion from the polymer network without dissolving the hydrogel. The electrolyte concentration should be sufficient to prevent polymer dissolution. Optionally, water-miscible solvents that inhibit hydrogel dissolution, such as acetone, a $C_1$–$C_4$ alcohol (e.g., methanol, ethanol, or propanol), or any other water-miscible reagent that is a solvent for the electrolyte but a non-solvent for the hydrogel, may be added to the aqueous electrolyte solution.

Preferred electrolytes are chlorides of monovalent cations, such as potassium, sodium, lithium, and hydrogen. An especially preferred electrolyte is potassium chloride. The electrolyte solution may optionally contain plasticizing ingredients, such as urea, glycerol, or sorbitol, e.g., to facilitate inter- and intra-chain motion during and after secondary shaping.

The gel density, which may be measured by solids level or polymer concentration, of the medical device may be suitably adjusted during the secondary-shaping step to achieve the mechanical properties desired. As gel density increases, higher strength and stiffness are typically obtained. Thermodynamic forces created in the electrolyte solution (and re-crosslinking solution) can be used, e.g., by adjusting the chemical concentration, to densify or swell the gel as desired.

Preferred electrolyte concentrations are from about one percent by weight to about the solubility limit of the electrolyte, and are more preferably about the solubility limit. The exposure (soaking) time, like the electrolyte concentration, is suitably selected to achieve the desired result. The electrolyte solution is preferably stirred or circulated during the crosslink-stripping step.

After the crosslink-stripping step and while still retaining the secondary shape, the hydrogel is re-crosslinked. Exemplary ionic crosslinkers for this include the crosslinking agents used in the original hydrogel composition. Preferred re-crosslinking solutions include aqueous solutions containing polyvalent metal cations such as calcium, strontium, lead, copper, aluminum, iron, tin, and barium ions. Mixtures of such ions can also be used in the re-crosslinking solution. Furthermore, the re-crosslinking ions can be changed during the secondary-shaping step, if desired. For example, calcium ions can be replaced by barium ions while the hydrogel is in a shaping device.

The re-crosslinking solution may optionally contain additives such as urea, glycerol, sorbitol, antiseptics, antibiotics, or fungicides, if desired. The concentration of the re-crosslinking solution also may be adjusted to provide osmotic shrinking or swelling forces during shaping and attain the desired gel density.

The various steps may be performed at any suitable temperature, e.g., at room temperature or under heating; preferably, the soaking is conducted at room temperature. Moreover, the steps may be performed one immediately after another, or a drying step (e.g., air-drying) may be interposed between one or more steps. Additionally, the shaped medical device may be sterilized after the sequence of secondary-shaping steps.

The medical device may be stored wet or dry. For example, the medical device may be stored in a suitable aqueous solution. Alternatively, the medical device may be dried for storage.

In preferred embodiments, secondary shaping is used to form elastically deformable retention features. For example, stents having pigtail-shaped retention features may be preshaped by extruding a hydrogel composition into the form of tubing and cutting the tubing into appropriate lengths. The tubing lengths are then subjected to secondary shaping by winding the ends of the tubing lengths under tension around the pins of a shaping jig, immersing the loaded jigs in an electrolyte solution to strip the composition of crosslinks, and immersing the jigs in a re-crosslinking solution.

Systems in which the medical devices of the invention are useful include cardiovascular, lymphatic, neurological, integumental, skeletal, muscular, optical, otorhinolaryngological, oral, gastrointestinal, and urogenital systems. Medical devices that may be made in accordance with the invention include ureteral, urethral, bilial, teal, and pyloric stents. Other exemplary medical devices include drainage devices (e.g., ear and sinus tubes), delivery devices, temporary plugs, and enteral feeding tubes and plugs. As evident from the following illustrative examples, deformable pigtail stents may be conveniently prepared at ambient temperature and pressure.

EXAMPLES

Example A

Part 1—Preparation of Preshaped Hydrogel

Calcium alginate having a tubing or cylindrical preshape is prepared. Specifically, to 95.10 grams of distilled water is added 5.005 grams of sodium alginic acid (Sigma, medium molecular weight, macrocystis pyrifera), followed by mixing until uniform (approximately 1 hour). The solution is heated to 90° C. for 45 minutes, cooled to room temperature, and then centrifuged to remove trapped air. The sodium alginic acid solution is then used to fill a 30-cc syringe, to which is connected a syringe pump and a peristaltic pump feed containing 10% by weight calcium chloride dihydrate in water. The syringe pump is used to wet-spin a tube of sodium-alginic acid into a crosslinking bath containing 10% by weight $CaCl_2$ dihydrate in water. After the tubing has been spun, the peristaltic pump is left on to maintain the flow of coagulant solution through the tube. After 30 minutes the tubing is removed from the crosslinking bath and placed in a 4 percent by weight aqueous $CaCl_2$ dihydrate solution. The tubing is left in this solution for 24 hours, and then cut into appropriate lengths.

Part 2—Secondary Shaping of Preshaped Hydrogel

The cut tubing is shaped into a double-pigtail ureteral stent configuration. First, the calcium alginate tubing is loaded onto a double-pigtail shaping jig (e.g., a Plexiglas plate having two pins affixed perpendicular to the plate, around which the ends of the cylindrical lengths are coiled or wound to form pigtail-shaped ends). The loaded jig is immersed into a solution of 25 percent by weight KCl in deionized water for 40 minutes. The shaping jig is removed from the KCl bath and immediately immersed into a solution of 30 percent by weight $CaCl_2 \cdot 2H_2O$ in deionized water.

The resulting calcium alginate stent will now permanently retain the double-pigtail configuration even in plasticizing environments, such as urine. Permanent loss of shape will not occur until the crosslinks are removed—e.g., via chemical triggering upon addition of a disintegration agent such as an inorganic sulfate, titrate or phosphate.

Example B

Part 1—Preparation of Preshaped Hydrogel

Sodium alginate (121.2 g of Pronova Protanal LF 10/60) is weighed into a 4"×5" (10 cm×13 cm) aluminum pan.

Deionized water (625.8 g) is weighed into a 1000-ml beaker. The beaker with water is placed under an overhead mixer, and the mixing blade is lowered off-center into the water. The mixer is operated at its highest speed to stir the water while the sodium alginate (Pronova Protanal LF 10/60) is quickly poured into the beaker.

After the sample is stirred for about 10 seconds, it is covered with Saran wrap and stored at room temperature in a hood overnight. The sample (718.2 g) is added to a Ross double planetary mixer, and the solution is mixed at 60° C. for 30 minutes. Then 54.1 g of bismuth subcarbonate are added, followed by mixing for an additional 30 minutes. The mixture is allowed to cool in the Ross mixer.

The mixture is loaded into sterile 30-cc syringes, and the syringes are centrifuged to remove entrapped air. The syringes are attached to a tubing die powered with a syringe pump, and tubing is extruded into a 30% calcium chloride dihydrate solution. The calcium chloride solution is also pumped through the center of the die as the tube is extruded. The tubing is left in the calcium solution overnight. The following day, the tubing is dialyzed in deionized water to remove excess ions. The tubing is cut into cylindrical lengths using a razor blade.

Part 2—Secondary Shaping of Preshaped Hydrogel

A length of cylindrical tubing is loaded onto a pigtail-shaping jig. The loaded jig is immersed in a solution of 25 percent by weight potassium chloride (KCl) in deionized water for 40 minutes. The shaping jig is removed from the electrolyte bath and directly immersed into a solution of 2.5 percent by weight $BaCl_2 \cdot 2H_2O$ bath with constant mixing. The jig is then placed into deionized water. After 30 minutes, the water is poured out and replaced with fresh deionized water. After another thirty minutes, the water is changed again. Thirty minutes later, the water is replaced with 3000 g of an aqueous 0.15% sodium sulfate solution. After 10 minutes in the $Na_2SO_4$ solution, the solution is poured out and replaced with fresh deionized water. This water is replaced after 30 total minutes has elapsed and again after 60 total minutes has elapsed. The shaped barium alginate pigtail stent is stored in deionized water. The resulting stent will permanently retain its elastic pigtail shape even when exposed to plasticizing body fluids.

Other embodiments of the invention will be apparent to those skilled in the art through consideration of the specification and practice of the invention disclosed herein. It is intended that the specification and examples be considered as exemplary only, with the true scope and spirit of the invention being indicated by the following claims.

What is claimed is:

1. A method for preparing a medical device comprising:
   (1) treating an ionically crosslinked hydrogel with a preliminary shape to strip an amount of the ionic crosslinks sufficient to erase the memory of the preliminary shape while retaining the hydrogel in a desired secondary shape, the treating being treatment with an electrolyte solution having sufficient electrolyte concentration to prevent polymer dissolution; and
   (2) ionically re-crosslinking the treated hydrogel of step (1) while retaining the hydrogel in the desired shape, to obtain a medical device, the amount of re-crosslinking being sufficient for secondary shape stability.

2. A method according to claim 1, wherein said ionically crosslinked hydrogel of step (1) has a tubular preshape.

3. A method according to claim 1, wherein said ionically crosslinked hydrogel of step (1) is formed from barium or calcium alginate.

4. A method according to claim 3, wherein said re-crosslinking step (2) comprises exposing the ionically crosslinked hydrogel to a re-crosslinking solution comprising water and a cationic crosslinker containing calcium, strontium, lead, copper, aluminum, iron, tin, or barium ions.

5. The method according to claim 1 wherein the hydrogel with a preliminary shape is tubular.

6. A method for preparing a medical device comprising:
   (1) forming a hydrogel with a preliminary shape from a composition comprising an ionically crosslinkable polymer and an ionic crosslinking agent; and
   (2) forming the hydrogel into a secondary shape by steps comprising:
      (a) imparting a secondary shape to the hydrogel,
      (b) stripping the hydrogel of sufficient crosslinks to erase the memory of the preliminary shape while retaining the secondary shape, said stripping comprising treatment with an electrolyte solution having sufficient electrolyte concentration to prevent polymer dissolution, and
      (c) re-crosslinking the hydrogel while retaining the secondary shape, to obtain a medical device, the amount of re-crosslinking being sufficient for secondary shape stability.

7. A method according to claim 6, wherein in step (1) said hydrogel is formed into a length of tubing.

8. A method according to claim 7, wherein said step (2)(a) comprises mounting said hydrogel in a shaping device.

9. A method according to claim 8, wherein said shaping device includes means for forming at least one coil or pigtail on the length of tubing.

10. The method according to claim 6 wherein the hydrogel with a preliminary shape is tubular.

11. A method according to claim 6, wherein said stripping step (2)(b) comprises immersing the mounted hydrogel in an electrolyte solution.

12. A method according to claim 11, wherein said electrolyte solution comprises water and potassium chloride.

13. A method according to claim 12, wherein the potassium chloride is present in the electrolyte solution in a concentration of about twenty-five percent by weight.

14. A method according to claim 12, wherein said electrolyte solution further comprises a plasticizer.

15. A method according to claim 14, wherein said plasticizer is urea, glycerol, or sorbitol.

16. A method according to claim 11, wherein the electrolyte solution is at about room temperature.

17. A method according to claim 11, wherein the electrolyte solution is agitated during the stripping step (2)(b).

18. A method according to claim 8, wherein said re-crosslinking step (2)(c) comprises immersing the mounted hydrogel in a re-crosslinking solution comprising water and an ionic crosslinker.

19. A method according to claim 18, wherein said polymer of the hydrogel composition is cationically crosslinkable and said ionic crosslinker contains ions selected from the group consisting of barium, calcium, magnesium, strontium, boron, beryllium, aluminum, iron, copper, cobalt, lead, tin, and silver ions.

20. A method according to claim 18, wherein said polymer of the hydrogel composition is anionically crosslinkable and said ionic crosslinker contains ions selected from the group consisting of phosphate, citrate, borate, succinate, maleate, adipate, and oxalate ions.

21. A method according to claim 18, wherein the re-crosslinking solution further comprises urea, glycerol, sorbitol, an antiseptic, an antibiotic, or a fungicide.

22. A method according to claim 6, wherein the forming step (2) is conducted at about room temperature.

23. A method according to claim 6, wherein said polymer is a polysaccharide.

24. A method according to claim 23, wherein said polysaccharide is a member selected from the group consisting of alginic acid, pectinic acid, hyaluronic acid, cellulose, chitosan, chitin, starch, dextran, heparin, chondroitin, cationic guar, cationic starch, carboxymethyl cellulose, carboxymethyl chitosan, carboxymethyl dextran, carboxymethyl starch, heparin sulfate, and chondroitin sulfate.

25. A method according to claim 23, wherein said polysaccharide is a member selected from the group consisting of alginic acid, pectinic acid, and hyaluronic acid, and their salts.

26. A method according to claim 25, wherein said ionic crosslinking agent is selected from the group consisting of barium, calcium, strontium, and copper ions.

27. A method according to claim 6, wherein the hydrogel composition further comprises a disintegrating agent.

28. A method according to claim 27, wherein the disintegrating agent is selected from the group consisting of inorganic sulfates, inorganic phosphates, and magnesium ions.

29. A method according to claim 6, wherein said polymer is alginic acid or a salt thereof, and said ionic crosslinking agent is barium or calcium ions.

30. A method according to claim 29, wherein the electrolyte solution comprises a solution of potassium, sodium, or lithium chloride, and said re-crosslinking step (2)(c) comprises immersing the hydrogel in a re-crosslinking solution comprising water and a cationic crosslinker containing calcium, strontium, lead, copper, aluminum, iron, tin, or barium ions while retaining the secondary shape, to re-crosslink the hydrogel to a degree sufficient for secondary shape stability.

31. A method according to claim 30, wherein said cationic crosslinker contains calcium or barium ions.

32. The method according to claim 1 wherein the electrolyte solution comprises a solution of potassium, sodium or lithium chloride.

33. The method according to claim 5 wherein the electrolyte solution has a concentration of about twenty-five percent potassium, sodium or lithium chloride based on the weight of the solution.

34. The method according to claim 1 wherein the re-crosslinking step (2) comprises treating the hydrogel of step (1) in a re-crosslinking solution comprising water and cationic crosslinker containing calcium, strontium, lead, copper, aluminum, iron, tin or barium ions.

35. The method according to claim 6 wherein the electrolyte solution comprises a solution of potassium, sodium or lithium chloride.

36. The method according to claim 33 wherein the electrolyte solution has a concentration of about twenty-five percent potassium, sodium or lithium chloride based on the weight of the solution.

37. The method according to claim 6 wherein the re-crosslinking step (2)(c) comprises treating the hydrogel of step (1) in a re-crosslinking solution comprising water and cationic crosslinker containing calcium, strontium, lead, copper, aluminum, iron, tin or barium ions.

38. The method according to claim 1 wherein the medical device is selected from the group consisting of stents, catheters, cannulas, plugs and restrictors.

39. The method according to claim 1 wherein the medical device is a stent.

40. The method according to claim 6 wherein the medical device is selected from the group consisting of stents, catheters, cannulas, plugs and restrictors.

41. The method according to claim 6 wherein the medical device is a stent.

42. The method according to claim 6 wherein the polymer is alginic acid or a salt thereof, the ionic crosslinking agent is barium or calcium ions, the stripping step (2)(b) comprises immersing the hydrogel in an electrolyte solution of potassium, sodium, or lithium chloride while retaining the secondary shape, the re-crosslinking step (2)(c) comprises immersing the hydrogel in a re-crosslinking solution comprising water and a cationic crosslinker containing calcium, strontium, lead, copper, aluminum, iron, tin, or barium ions, and the medical device is selected from the group consisting of stents, catheters, cannulas, plugs and restrictors.

* * * * *

UNITED STATES PATENT AND TRADEMARK OFFICE
CERTIFICATE OF CORRECTION

PATENT NO. : 5,718,862
DATED : February 17, 1998
INVENTOR(S) : Samuel Anthony Thompson It is certified that error appears in the above-identified patent and that said Letters Patent is hereby corrected as shown below:

Column 6, line 42 after and ethylene replace "dime" with --diamine--.
Column 8, line 63 after inorganic sulfate replace "titrate" with --citrate--.

Signed and Sealed this

Fifth Day of January, 1999

Attest:

Attesting Officer

*Acting Commissioner of Patents and Trademarks*